United States Patent [19]

Forbes

[11] Patent Number: 5,756,883
[45] Date of Patent: May 26, 1998

[54] METHOD OF CONTINUOUSLY TESTING THE ACCURACY OF RESULTS OBTAINED FROM AN AUTOMATIC VISCOMETER

[75] Inventor: David Wesley Forbes, Edmonton, Canada

[73] Assignee: The Fluid Corporation, Edmonton, Canada

[21] Appl. No.: 674,267

[22] Filed: Jul. 1, 1996

Related U.S. Application Data

[63] Continuation of Ser. No. 444,682, May 19, 1995, abandoned.

[51] Int. Cl.$^6$ .................................................. G01N 11/04
[52] U.S. Cl. ...................... 73/54.05; 73/54.04; 73/54.07; 73/1 R
[58] Field of Search .......................... 73/54.01, 54.04, 73/54.05, 54.06, 54.07, 54.08, 1 R

[56] References Cited

U.S. PATENT DOCUMENTS

| | | | |
|---|---|---|---|
| 3,005,552 | 10/1961 | Müller | 73/54.05 |
| 3,026,705 | 3/1962 | Blackman et al. | 73/1 R |
| 3,610,026 | 10/1971 | Topham | 73/54.06 |
| 3,713,328 | 1/1973 | Aritomi | 73/55 |
| 3,798,960 | 3/1974 | Glass | 73/55 |
| 3,808,877 | 5/1974 | Blair | 73/54.06 |
| 3,895,513 | 7/1975 | Richardson | 73/55 |
| 4,167,245 | 9/1979 | Kock et al. | 239/11 |
| 4,384,472 | 5/1983 | Tournier | 73/54.06 |
| 4,463,598 | 8/1984 | Haney | 73/55 |
| 4,616,503 | 10/1986 | Plungis et al. | 73/55 |

OTHER PUBLICATIONS

Article "A Simple, Cost-Effective Automatic Capillary Viscometer System" published in Journal of Polymer Science, Polymer Physics Edition, vol. 21, 1559–1572 (1983).

Article "Automatic Capillary Viscometer for Fluids with Variable Opacity" published by 1988 American Institute of Physics Rev. Sci. Instrum.59(10), Oct. 1988.

*Primary Examiner*—Hezron E. Williams
*Assistant Examiner*—Jay L. Politzer
*Attorney, Agent, or Firm*—Anthony R. Lambert

[57] ABSTRACT

A method of testing the accuracy of results obtained from an automatic viscometer is described. Firstly, provide an automatic viscometer having at least two capillary tube test sections, each of a distinct uniform diameter. Secondly, calibrate the automatic viscometer by allowing a Newtonian fluid of known viscosity to flow through each of the capillary tube test sections and recording the time duration of the flow of the Newtonian fluid through each of the capillary tube test sections. Thirdly, calculate a viscosity constant for each capillary tube test section by dividing the known viscosity by the recorded flow time. Fourthly, send a test sample through each of the capillary tube test sections and record the time duration of the flow of the test sample through each of the capillary tube test sections. Fifthly, calculate values for the viscosity of the test sample based upon the times recorded and the known viscosity constant for each of the at least two capillary tube test sections. Sixthly, compare the viscosity measurement derived from each of at least two capillary tube test sections. A difference in viscosity measurement exceeding a predetermined limit indicating that the measurement is suspect and the accuracy of the automatic viscometer must be checked as the test sample is exhibiting non-newtonian behavior.

2 Claims, 3 Drawing Sheets

METHOD OF CONTINUOUSLY TESTING THE ACCURACY OF RESULTS OBTAINED FROM AN AUTOMATIC VISCOMETER

This is a continuation of application Ser. No. 08/444,682 filed May 19, 1995 now abandoned.

FIELD OF THE INVENTION

The present invention relates to a method of continually testing the accuracy of results obtained from an automatic viscometer, and in particular, indicating when the measurement is suspect and the apparatus may be in need of a vigorous cleaning to regain calibration.

BACKGROUND OF THE INVENTION

A viscometer measures the viscosity of liquids. Viscosity is a measurement of the resistance to flow. A common measure of this resistance to flow is kinematic viscosity. Section 5 of the ASTM handbooks covers standards for petroleum products and lubricants. A recognized test method for performing this measurement is designated ASTM D445-88, that calls for a liquid to be tested by flowing through a single bore glass capillary tube. There are a number of factors, however, that can adversely affect the results obtained.

One factor that adversely affects test results is the cleanliness of the testing equipment. Many types of lubricant samples will leave a thin deposit of insoluble material on the walls of the glassware. These deposits accumulate after repeated use resulting in inaccurate viscosity results. In a laboratory testing used lubricants, such accumulation may occur quickly. An accuracy check of the viscometer tube may have to be performed every few samples. If there are a large number of samples to measure, these quality assurance checks become prohibitively frequent and expensive. The method to clean glassware is prescribed in ASTM-D445 section 12.2. Periodic cleaning with strong acids is called for when the tube falls out of calibration. The method suggests 12 hours minimum cleaning time. This is impractical to perform very often. In fact, even with cleaning every few samples, it may be impractical to guarantee that the tube is cleaned properly and within specifications for every test sample measured. The rate of build up depends heavily on the source of the samples. For instance when measuring viscosity of used diesel engine oil, a tube may go out of calibration very quickly. Other types of lubricants may rarely leave deposits. Unless quality assurance procedures are in place, there is no idea how far out of calibration a tube has strayed before proper cleaning. The ASTM D445 method requires that a sample be measured twice and results compared. If the tube is out of calibration, two inaccurate measurements will be obtained, but they will fall within the repeatability limits and an inaccurate result arrived at.

A second factor that affects the test results is the presence of non-Newtonian fluid. ASTM D445 section 1.2 limits the scope of the test method to Newtonian fluids. If a fluid in non-Newtonian, it is important to determine this fact as the test results will be invalid. A Newtonian fluid can become non-Newtonian with use. For example, diesel engine lubricant can become non-Newtonian as a result of accumulating products of combustion.

A third factor affecting results are the presence of dissolved gases or volatile constituents. These result in varying pressure on the fluid as it is flowing. If the temperature of the fluid is heated near 100 C.; any water in the sample will vaporize inflicting the same problem. These may lead to inaccurate results, especially in automated equipment unable to detect these conditions.

There has been a tendency in recent years to increase the number of samples that can be tested per hour by constructing viscometers that are capable of making viscosity measurements in a fraction of the time the ASTM-D445 method requires. In order to do this equipment designers reduce the sample volume requirements for each test. A reduced sample volume has an advantage in that the smaller volume sample can acquire a uniform temperature more rapidly. Electronic meniscus sensors and timers allow accurate measurement of short flow times and are well known to the art. Such designs are totally automated, complete with a solvent based cleaning and drying scheme. However, residual fluid from a previous test or solvent liquid or vapour present from improper cleaning have a much larger impact on accuracy when a small sample volume is used. A malfunction in the automated equipment could render all subsequent tests results invalid.

SUMMARY OF THE INVENTION

What is required is a viscometer tube configuration that is sensitive to the factors that cause inaccurate measurements.

According to the present invention there is provided a method of testing the accuracy of results obtained from an automatic viscometer. Firstly, provide an automatic viscometer having at least two capillary tube test sections, each of a distinct uniform diameter. Secondly, calibrate the automatic viscometer by allowing a Newtonian fluid of known viscosity to flow through each of the capillary tube test sections and recording the time duration of the flow of the Newtonian fluid through each of the capillary tube test sections. Thirdly, calculate a viscosity constant for each capillary tube test section by dividing the known viscosity by the recorded flow time. Fourthly, send a test sample through each of the capillary tube test sections and record the time duration of the flow of the test sample through each of the capillary tube test sections. Fifthly, calculate values for the viscosity of the test sample based upon the times recorded and the known viscosity constant for each of the at least two capillary tube test sections. Sixthly, compare the viscosity measurement derived from each of at least two capillary tube test sections. A difference in viscosity measurement exceeding a predetermined limit indicating that the measurement is suspect and the accuracy of the automatic viscometer must be checked as the test sample is exhibiting non-newtonian behaviour.

When the above described method is used, the automatic viscometer alerts the operator when a comparison of test results indicates that either the equipment is in need of cleaning or the sample that is being tested is contaminated to such an extent that non-Newtonian behaviour is being exhibited.

Although beneficial results may be obtained through the use of the method, as described above, it is desirable to maximize the number of samples that can be processed in a working day. Even more beneficial results may, therefore, be obtained when the capillary tube test sections are vertically aligned, such that the fluid sample passes through the capillary tube test sections sequentially with each succeeding a capillary tube test section being a smaller diameter than the prior capillary tube test section.

The refinement to the method involves joining capillary sections of differing bores such that the fluid passes through each successively. The fluid must pass through the largest bore first with each section becoming successively smaller in diameter. The minimum requirement entails two different bore sizes, but more is certainly possible. The diameters of the bores may be chosen such that the flow of fluid is laminar within each bore. Appropriate efflux or influx reservoirs may be included in the configuration as requirements dictate. Timing marks or meniscus sensors are required for measuring the flow time for each different bore.

To calibrate the apparatus, a Newtonian fluid of known viscosity is allowed to pass through the apparatus while timings are recorded. The viscosity constant for each capillary section is calculated by dividing the known viscosity by the flow time. Viscosity of an unknown Newtonian fluid may then be calculated by multiplying the respective measured times by the viscosity constants. One finds the calculated viscosities are equivalent.

Since the viscosity constant for a particular capillary is a function of the cross sectional area of the bore, the constant will change as build up is deposited on the capillary walls. Assuming a uniform thickness coating on a bore, the reduction in cross sectional area filled in by the coating is a function of the bore's diameter. If we apply a thin, uniform coating to two bores of differing diameter, one finds the viscosity constant changes with differing ratios for the two bores. Should the bores start accumulating deposits, we will note a difference in the calculated viscosity for each capillary section. When the difference in calculated viscosity exceeds a limit, this signals that the viscosity constants are no longer within the required accuracy.

With this configuration, the fact that a fluid is non-Newtonian may be confirmed. Each different bore capillary section will provide differing viscosity results. This can now be determined in one pass through the apparatus.

The configuration of multiple capillary sections each with different bores can detect if this contamination is present. As the sample is flowing through the contaminated apparatus, the viscosity changes as contaminants mix with the sample. A viscosity is calculated from the first capillary section. The sample continues flowing, picking up additional contaminants. The viscosity measured in the next capillary section will be different than the first. This fact would allow the measurement to be suspect.

This multiple bore configuration described is particularly suited to automated viscometers which require a means to detect when results are suspect. If the driving force causing the fluid to flow through the apparatus is constantly changing due to dissolved gases being released from the sample, or water boiling out of a sample, it is not possible to calculate an accurate viscosity. This condition will very likely yield wildly differing results through the different capillary sections in the proposed configuration.

There are several other conditions detectable with the new configuration. These include partial blockages in one or more capillary sections, presence of solids in the fluid causing it to become non-Newtonian, and large particles in the sample temporarily restricting the bore or air bubbles making their way through the capillary.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

The preferred method of testing the accuracy of results obtained from an automatic viscometer will now be described with reference to FIGS. 1 through 4.

The automatic viscometer illustrated is intended to demonstrate how the teachings of the method can be incorporated into automatic viscometer equipment.

Figure 1:
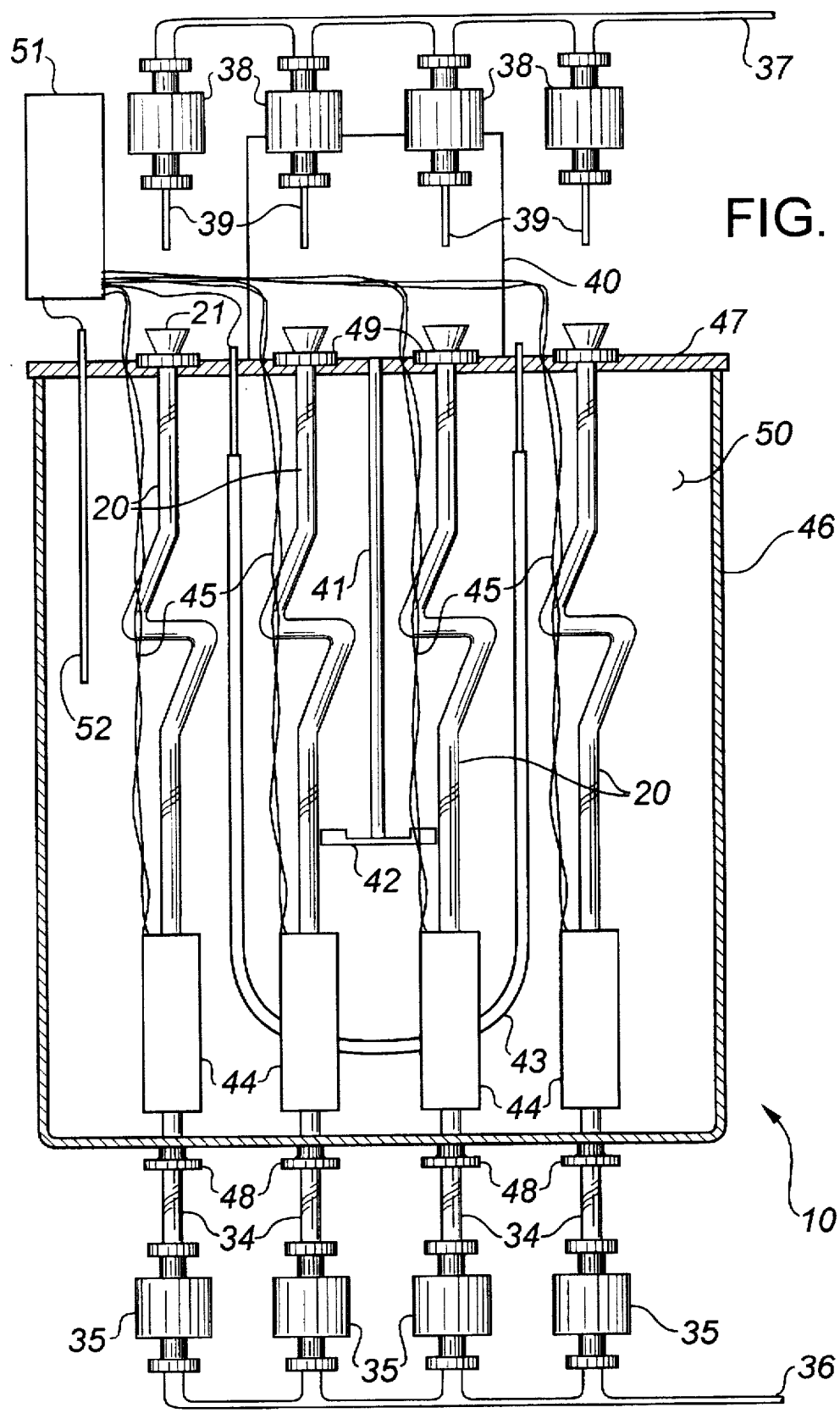
FIG. 1 is a side elevation view in section of a viscometer constructed in accordance with the teachings of the present invention.
Figure 2:
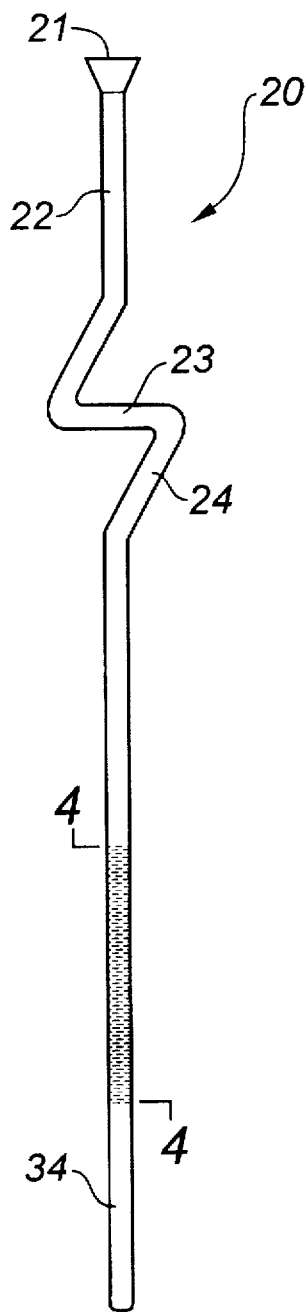
FIG. 2 is a side elevation view of a single capillary tube from the viscometer illustrated in FIG. 1.
Figure 3:
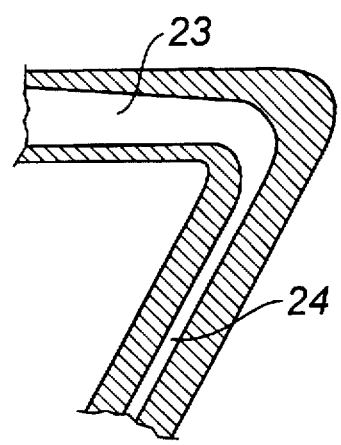
FIG. 3 is a detailed side elevation view of a bent portion of the capillary tube illustrated in FIG. 2.
Figure 4:
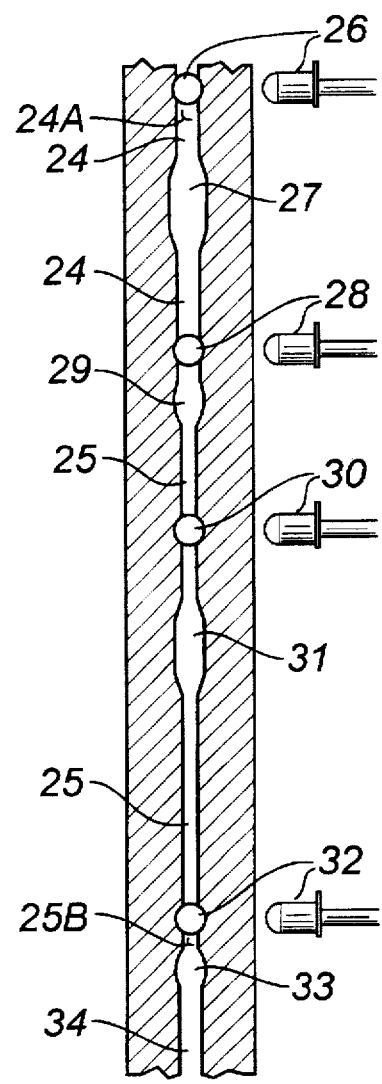
FIG. 4 is a detailed side elevation view of a straight portion of the capillary tube taken along section line 4—4 FIG. 2.

Referring to FIG. 1, there is illustrated an automatic viscometer, generally identified by reference numeral 10. Automatic viscometer 10 obtains multiple measurements from a single sample of fluid. Referring to FIG. 2, the sample to be measured is first introduced to the glass viscometer tube 20 at the entrance funnel 21. Referring to FIG. 1, a vent-vacuum 3 way solenoid valve 35 is positioned to vent to atmosphere, allowing the sample to flow freely into the delivery tube 22. The sample begins to acquire the same temperature as the bath fluid 50. Referring to FIG. 2, the delivery tube 22 bends and forms a horizontal section 23 and is joined to the larger capillary tube 24. This is clearly shown in FIG. 3. The velocity of the fluid through the horizontal section is much slower than through the delivery tube allowing the sample time to acquire the same temperature as the bath fluid 50. Referring to FIG. 4, the sample flows through the larger capillary 24 restricted only by the bore size. When the meniscus of the sample reaches timer start meniscus sensor 26 positioned adjacent entry bore 24a of larger capillary 24, the computer 51 (as illustrated in FIG. 1) begins counting time. The sample flows through the influx reservoir 27 and then the meniscus passes larger capillary timer stop meniscus sensor 28 positioned adjacent exit bore 24b of larger capillary 24 at which point timing is stopped. The computer 51 then calculates the first viscosity measurement from the measured time. The sample continues flowing, through the larger capillary to smaller capillary joint 29 into the smaller capillary 25 where the flow is only restricted by the bore size of the smaller capillary 25. When the meniscus of the sample reaches smaller bore timer start meniscus sensor 30 positioned adjacent entry bore 25a of smaller capillary 25, the computer 51 begins counting time. The sample flows through the influx reservoir 31 and then the meniscus passes smaller capillary timer stop meniscus sensor 32 positioned adjacent exit bore 25b of smaller capillary 25 at which point timing is stopped. The computer 51 then calculates the second viscosity measurement from the measured time. The computer 51 compares the first and second viscosity measurement to determine the validity and returns a result. Referring to FIG. 1, the cleaning process begins with the computer 51 causing solvent delivery solenoid valve to allow a quantity of solvent to flow from the solvent supply 37 to the solvent delivery tube 39. The solvent enters the viscometer tube 20 at the entrance funnel 21. The computer 51 then causes the vent-vacuum 3 way solenoid valve 35 to apply vacuum from the vacuum supply 36 to the exit tube 34. Most of the sample is drawn out of the viscometer tube 20. The computer 51 then causes the solvent delivery solenoid valve 38 and vent-vacuum 3 way solenoid valve to operate repeatedly until all the sample is drawn out the vacuum supply 36. The computer 51 then causes the vent-vacuum 3 way solenoid valve 35 to apply vacuum from the vacuum supply 36 to the exit tube 34 until all traces of the solvent are evaporated and drawn out of the viscometer tube 20. The computer 51 then causes the vent-vacuum 3 way solenoid valve to apply a vent to atmosphere to the exit tube 34 in preparation for the next sample.

The computer 51 waits a predetermined amount of time to allow the viscometer tube 20 to acquire the same temperature as the bath fluid 50 before requesting the next sample. The bath fluid 50 is held in the constant temperature bath housing 46. The fluid is continuously circulated by an impeller 42, turned by a motor drive shaft 41 connected to a motor 40. The temperature of the bath fluid is held constant by an electric heating element 43 and temperature sensor 52; both of which are connected to computer 51. The viscometer tube 20 is held in place by a top seal 49 in the constant temperature bath top 47, and a exit tube seal 48. Seals 48 and 49 are removable such that the viscometer tube 20 may be removed from the viscometer 10. The meniscus sensors 26, 28, 30, and 32 (as illustrated in FIG. 4) are held within the meniscus sensor housing 44 (as illustrated in FIG. 1) which is affixed to the viscometer tube 20. The meniscus sensor signal wiring 45 carries the electrical signals through the delivery tube seal 49 to the computer 51.

In operation, computer 51 alerts the operator should the difference in viscosity measurement exceed a predetermined limit. The operator can be alerted in various ways, such as an auditory alarm. The operator, knowing the test sample is exhibiting non-newtonian behaviour, can then check both the test sample and the equipment. Either the test sample is a non-Newtonian fluid, or the automatic viscometer is not operating within desired tolerances due to contamination.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. A method of testing the accuracy of results obtained from an automatic viscometer, comprising the steps of:

firstly, providing an automatic viscometer having at least two capillary tube test sections, each capillary tube having an entry bore and an exit bore, the entry bore and exit bore being of the same diameter, the entry bore and the exit bore of each of the at least two capillary tube test sections having a distinct uniform diameter, each of the at least two capillary tube test sections having a time start sensor and a time stop sensor positioned in spaced relation with the time start sensor positioned closer to the entry bore than the time stop sensor;

secondly, calibrating the automatic viscometer by allowing a Newtonian fluid of known viscosity to flow through each of the capillary tube test sections and recording the time duration of the flow of the Newtonian fluid through each of the capillary tube test sections;

thirdly, calculating a viscosity constant for each capillary tube test section by dividing the known viscosity by the recorded flow time;

fourthly, sending a test sample through each of the capillary tube test sections and recording the time duration of the flow o f the test sample through each of the capillary tube test sections;

fifthly, calculating values for the viscosity of the test sample based upon the times recorded and the known viscosity constant for each of the at least two capillary tube test sections; and sixthly, comparing the viscosity measurement derived from each of at least two capillary tube test sections, a difference in viscosity measurement exceeding a predetermined limit indicating that the measurement is suspect and the accuracy of the automatic viscometer must be checked as the test sample is exhibiting non-newtonian behaviour.

2. An automatic viscometer, comprising:

at least two capillary tube test sections, each capillary tube having an entry bore and an exit bore, the entry bore and exit bore being of the same diameter, the entry bore and the exit bore of each of the at least two capillary tube test sections having a distinct uniform diameter, and being vertically aligned, such that a fluid sample passes sequentially through the at least two capillary tube test sections, the entry bore and the exit bore of each succeeding capillary tube test section being a smaller diameter than the entry bore and the exit bore of the prior capillary tube test section;

means for heating a test sample fluid in preparation for testing;

each of the at least two capillary tube test sections having a time start sensor and a time stop sensor positioned in spaced relation with the time start sensor positioned closer to the entry bore than the time stop sensor;

a computer connected to the time start sensor and time stop sensor of each of the at least two capillary tube test sections, such that when the test sample flows sequentially through each of the capillary tube test sections, the computer receives signals from the time start sensor and time stop sensor in each of the at least two capillary tube test sections, thereby recording the time duration of the flow of the test sample through each of the capillary tube test sections; and the computer being programmed to calculate values for the viscosity of the test sample based upon the times recorded and a known viscosity constant for each of the at least two capillary tube test sections, compare the viscosity measurement derived from each of at least two capillary tube test sections and alert the operator should the comparison disclose a difference in viscosity measurement exceeding a predetermined limit.

* * * * *

UNITED STATES PATENT AND TRADEMARK OFFICE
CERTIFICATE OF CORRECTION

PATENT NO. : 5,756,883
DATED : May 26, 1998
INVENTOR(S) : David Wesley Forbes

It is certified that error appears in the above-indentified patent and that said Letters Patent is hereby corrected as shown below:

On the title page,
Item [73] Assignee: "The Fluid Corporation, Edmonton, Canada" is amended to read --The Fluid Life Corporation, Edmonton, Canada--

Signed and Sealed this

Twentieth Day of July, 1999

Attest:

Q. TODD DICKINSON

*Attesting Officer*        Acting Commissioner of Patents and Trademarks